(12) United States Patent
Pond

(10) Patent No.: US 7,431,587 B2
(45) Date of Patent: Oct. 7, 2008

(54) DENTAL TOOL ADAPTOR ASSEMBLY

(76) Inventor: Gary J. Pond, 2816 N. Main St., Racine, WI (US) 53402

( * ) Notice: Subject to any disclaimer, the term of this patent is extended or adjusted under 35 U.S.C. 154(b) by 26 days.

(21) Appl. No.: 10/981,380

(22) Filed: Nov. 4, 2004

(65) Prior Publication Data

US 2006/0024639 A1   Feb. 2, 2006

Related U.S. Application Data

(60) Provisional application No. 60/592,722, filed on Jul. 30, 2004.

(51) Int. Cl.
*A61C 17/00* (2006.01)
(52) U.S. Cl. .......................... 433/80; 604/241
(58) Field of Classification Search .................. 433/80, 433/126; 604/241, 243
See application file for complete search history.

(56) References Cited

U.S. PATENT DOCUMENTS

| | | | |
|---|---|---|---|
| 1,417,379 A | 5/1922 | Harvin | |
| 1,958,332 A | 5/1934 | Carpenter | |
| 3,745,655 A | 7/1973 | Malmin | |
| 3,874,083 A * | 4/1975 | Buckley | 433/80 |
| 3,949,748 A | 4/1976 | Malmin | |
| 3,972,121 A | 8/1976 | Nash | |
| 3,974,831 A | 8/1976 | Malmin | |
| 4,068,664 A | 1/1978 | Sharp et al. | |
| 4,187,848 A * | 2/1980 | Taylor | 604/243 |
| 4,248,589 A | 2/1981 | Lewis | |
| 4,346,703 A * | 8/1982 | Dennehey et al. | 604/406 |
| 4,353,693 A | 10/1982 | Dery et al. | |
| 4,384,852 A | 5/1983 | Yamauchi et al. | |
| 4,762,150 A | 8/1988 | Kokuryu | |
| 4,810,194 A | 3/1989 | Snedden | |
| 4,822,278 A | 4/1989 | Oliva et al. | |
| 4,878,900 A | 11/1989 | Sundt | |
| 4,915,135 A | 4/1990 | Kellenbarger et al. | |
| 5,013,300 A | 5/1991 | Williams | |
| 5,033,961 A | 7/1991 | Kandler et al. | |
| 5,049,071 A | 9/1991 | Davis et al. | |
| 5,234,338 A | 8/1993 | Young | |
| 5,378,149 A | 1/1995 | Stropko | |
| 5,402,821 A | 4/1995 | Harstad | |
| 5,489,205 A | 2/1996 | Davis et al. | |
| 5,592,974 A | 1/1997 | Grobs et al. | |
| 5,927,975 A * | 7/1999 | Esrock | 433/80 |
| 6,119,728 A | 9/2000 | Seidel-Peschmann et al. | |
| 6,149,429 A * | 11/2000 | Bukowski et al. | 433/80 |
| 6,238,211 B1 * | 5/2001 | Esrock | 433/80 |
| 6,450,810 B1 * | 9/2002 | Fischer et al. | 433/80 |
| 6,510,970 B2 * | 1/2003 | McLean et al. | 222/527 |
| 2004/0072123 A1 * | 4/2004 | Simonton et al. | 433/80 |

* cited by examiner

*Primary Examiner*—Ralph A Lewis
(74) *Attorney, Agent, or Firm*—Ryan Kromholz & Manion, S.C.

(57) ABSTRACT

A disposable extension member for joining a dental handtool to a disposable, hollow, dental tip. The dental handtool includes a chuck for releasably retaining the extension member. The extension member has at least one fluid-tight passageway extending through its body for fluid flow from the dental handpiece to the dental tip. The extension member includes an adaptive releasable locking member having an internally threaded, cuplike end portion dimensioned for releasable threading engagement with the dental tip. The chuck provides easy and efficient clamping means to secure the extension member within the handtool.

2 Claims, 5 Drawing Sheets

DENTAL TOOL ADAPTOR ASSEMBLY

RELATED APPLICATIONS

This application claims the benefit of provisional patent application Ser. No. 60/592,722 filed 30 Jul. 2004.

BACKGROUND OF THE INVENTION

The present invention relates to dental syringe adaptors, and more specifically to disposable dental syringe adaptors capable of providing both air and water and that may be quickly inserted or removed from a dental tool.

Dental syringes are widely used by dentists, dental assistants, dental hygienists and similar personnel. The syringes are generally handheld devices that deliver air and water to a patient's mouth during dental procedures. Examples of such syringes are found in U.S. Pat. Nos. 5,378,149 and 4,248,589. The devices generally selectively deliver the air and water at a predetermined pressure. Valves in the dental instrument allow for selective control of the water or air discharge.

Cross contamination is a principal concern with dental syringes and dental procedures, in general. Because it is not desirous to transmit or pass bacteria and/or viruses from one patient to another, syringes, tips, and extension pieces have been developed that are autoclavable. Specifically, these devices are made of stainless steel, which can become quite expensive. Extension members, in particular, are expensive, especially if the extension members are designed for a single style of handpiece, such as an air/water syringe or just a water syringe. A disposable extension member would significantly reduce the costs of dental procedures.

U.S. Pat. No. 5,049,071, discloses a plastic dental syringe that is adaptable to a handheld dental tool. The syringe may be used as an air/water syringe. However, the design of the syringe does not allow adaptation between different styles or types of dental tips. The syringe is designed for a single type of use. Thus, the disclosed syringe may be not necessarily be used for different procedures that require different dental tips, and the utility of the syringe is limited.

Furthermore, it is desirous for dental tools and dental tips to adapt easily to each other. Such results may be achieved by using a locking device for syringes and adaptors that quickly and easily join the dental tools to the dental tips. It would be further desirous to develop a disposable extension member for releasably receiving and connecting with syringe tips that provides for expanded use of such locking devices and for quick exchange of dental accessories.

SUMMARY OF THE INVENTION

The present invention provides an adaptor assembly for connecting a dental tip to a dental handpiece. More specifically, the present invention provides a disposable extension member for connecting a dental tip to a dental handpiece. The extension member has a first end portion that will be releasably retained within a head portion of the dental handpiece by a chuck assembly. A second end portion has an internally threaded cuplike member that allows the dental tip to be threaded onto the extension member. The extension member is ideal for use with threadable dental tips, such as LUER-LOK® style dental tips. The extension member has a through passageway, which allows fluid to pass from the dental handpiece to the dental tip. The arrangement of the first end portion with the chuck and the second end portion with the cuplike member provides a fluid tight seal for the extension member.

Because the extension member is disposable, the member significantly reduces the costs of dental procedures. Also, time is reduced, since the extension member does not need to be autoclaved, but may be thrown out after use. Furthermore, the extension member can be designed to work with a handpiece that delivers water, air, or both, which will further reduce costs in that several different autoclavable extension members may be replaced with the present invention.

The present invention is also advantageous in that it can be used with a wide variety of adaptor assemblies, which also have novel features that will described in further detail with following specification and drawings.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
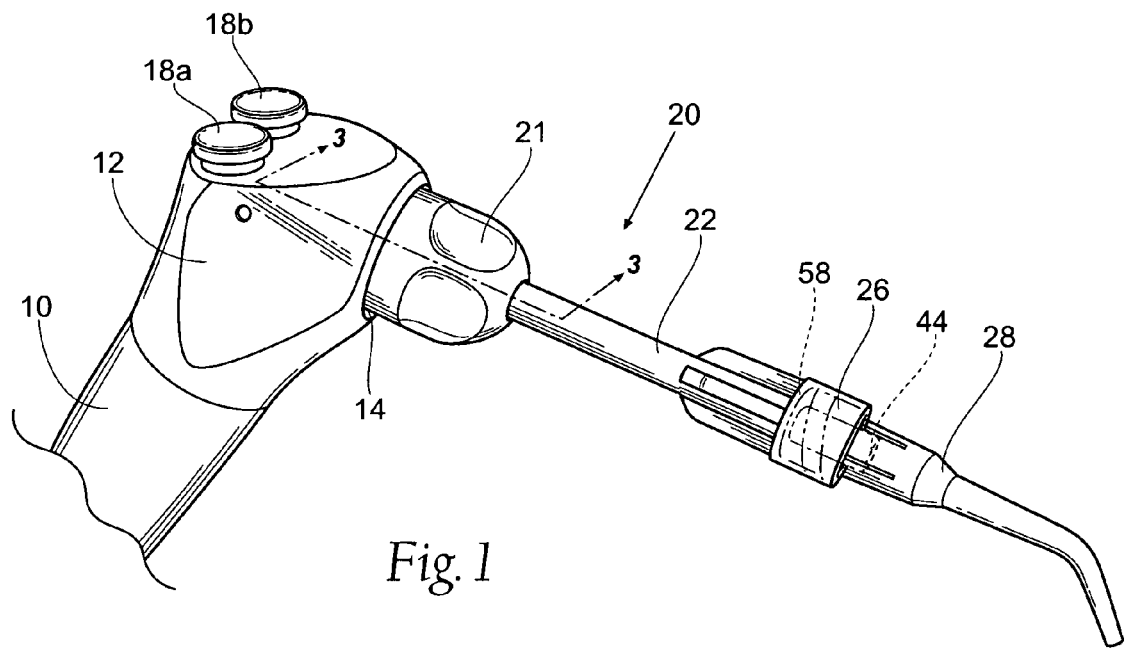
FIG. 1 is a perspective view of a dental handpiece used for aspiration of air and/or water and including an adaptor assembly according to the present invention.

FIG. 1 shows a perspective view of a dental handpiece 10 including an adaptor assembly 20. The adaptor assembly 20 includes a chuck 21 and an elongate extension member 22. The dental handpiece 10 has a head portion 12 with a reentrant socket 14 (see FIG. 3) located within the head portion 12. The socket 14 is arranged to receive an inwardly extending portion of the chuck 21 and the extension member 22 so that the extension member 22 will be fittingly secured to the dental handpiece 10. The handpiece 10 has a through passageway 16 (see FIG. 3) that is in fluid communication with the extension member 22. The head portion 12 includes finger valves 18a and 18b for control of air and water flow, respectively. While the dental handpiece 10 is arranged to receive both water and air, the present invention will work with handpieces that deliver only water or air, or other possible fluids. As will be evident with reference to the further drawings and description of the application, the extension member 22 may be easily removed from the handpiece 10 when necessary. The extension member 22 preferably comprises an elongated body having a first end portion 24 that interacts with the socket 14 and the chuck 21, and a second end portion 26 that allows a dental tip or needle 28 to be attached to the extension member 22. As will be discussed in more detail with respect to FIG. 8, the extension member 22 is arranged so that a disposable dental tip 28 may be removably attached to the second end portion 26 of the extension member 22.

Figure 2:
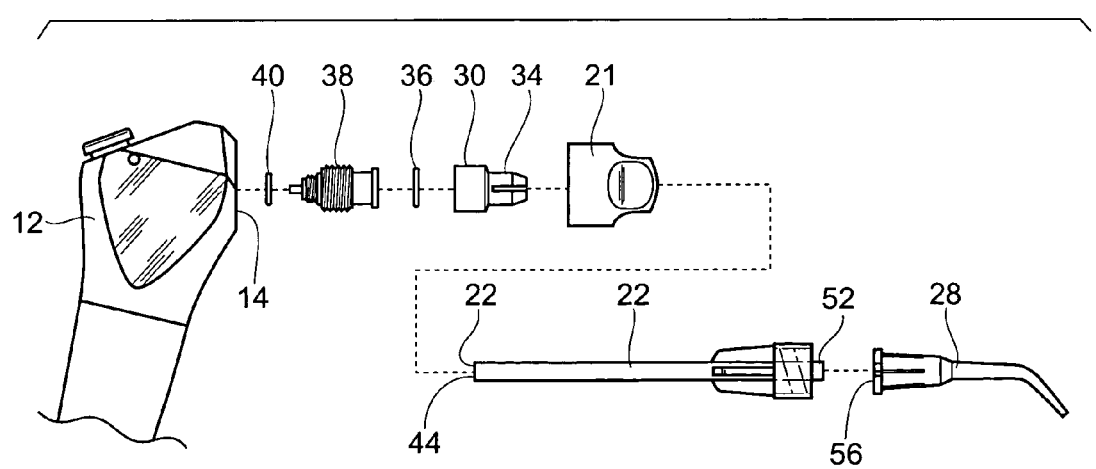
FIG. 2 is an exploded view of the adaptor assembly shown in FIG. 1.

FIG. 2 shows an exploded view of the adaptor assembly 20. The adaptor assembly 20 comprises the chuck 21 and an annular collet 30. The chuck 21 includes a plurality of circumferentially spaced, externally tapered jaws 34, which will allow the extension member 22 to be clamped within the chuck 21. The collet 30 and the jaws 34 are preferably designed of a resilient plastic so that they will grasp the extension member 22 securely and with enough resistance to firmly retain the extension member 22 within the chuck 21, without damaging the extension member 22. A first O-ring 36 sits between the chuck 21 and an externally threaded coupling member 38 to provide a fluid sealing connection between the chuck 21 and the threaded section 38. Any suitable sealing means may be used in place of the first O-ring 36 that allows a fluid tight connection between the externally threaded coupling member 38 and the chuck 21. The externally threaded coupling member 38 will sit within a second O-ring 40 located within the socket 14 to provide a fluid tight throughbore between the dental tool 10 and the externally threaded coupling member 38.

Figure 3:
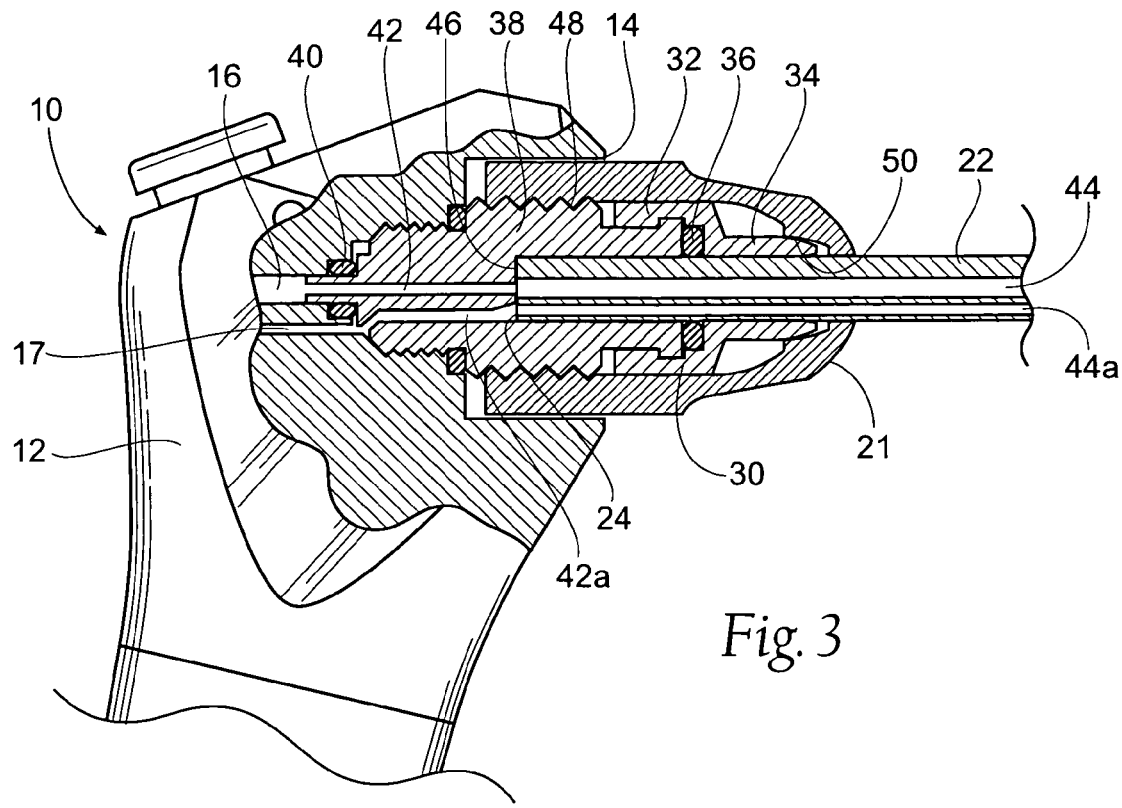
FIG. 3 is a partially cut-away side view taken along line 3-3 of FIG. 1 showing operating components of the dental handpiece and in operating connection with the adaptor assembly fabricated according to the present invention.

FIG. 3 is a partially cut-away view of the socket 14 of the dental handpiece 10 housing the chuck 21. As previously noted, the chuck 21 is arranged to securely retain the extension member 22 within the socket 14. The adaptor provides fluid communication from the fluid source through the passageway 16 located within the handpiece 10 to the extension member 22 by way of a throughbore or through passageway 42 located in the threaded externally threaded coupling member 38. A secondary passageway 17 is also located within the handpiece 10. The passageway 17 would be utilized if the handpiece 10 used for delivering a second fluid, such as air. The throughbore 42 is in communication with a passageway 44 located in the extension member 22. As shown in FIG. 3, a secondary throughbore 42a, and a secondary passageway 44a are in communication as well. The secondary throughbore 42a and passageway 44a may be used to deliver an air flow to the dental tip. They are not necessary for the present invention, but show that the extension member 22 may be used and adapted for a dental tool having any number of fluid passageways and arrangements.

Still referring to FIG. 3, the first end 24 of the extension member 22 is inserted into the chuck 21 until it rests firmly upon an extending edge 46 of the coupling member 38. Once fully inserted, a threaded section 48 of the collet 30 will be threaded onto the externally threaded coupling member 38. The collet 30, which has an internal tapered surface 50, will compress the tapered jaws 34 of the chuck 21 to thereby firmly retain the extension member 22. The abutment of the first end 24 of the extension member 22 with the extending edge 46 will form a tight seal, but the first O-ring 36 is preferably used to further maintain the fluid tight seal between the extension member 22 and the chuck 21.

It should be understood that FIG. 3 is merely exemplary of adaptor arrangements and should not be considered limiting. The disposable extension member 22 is designed to provide a sealing arrangement with different dental handpieces and further allow connection to a dental tip in an efficient manner, and should include similarly arranged designs that will provide a fluid tight arrangement with a disposable extension member.

Figure 4:
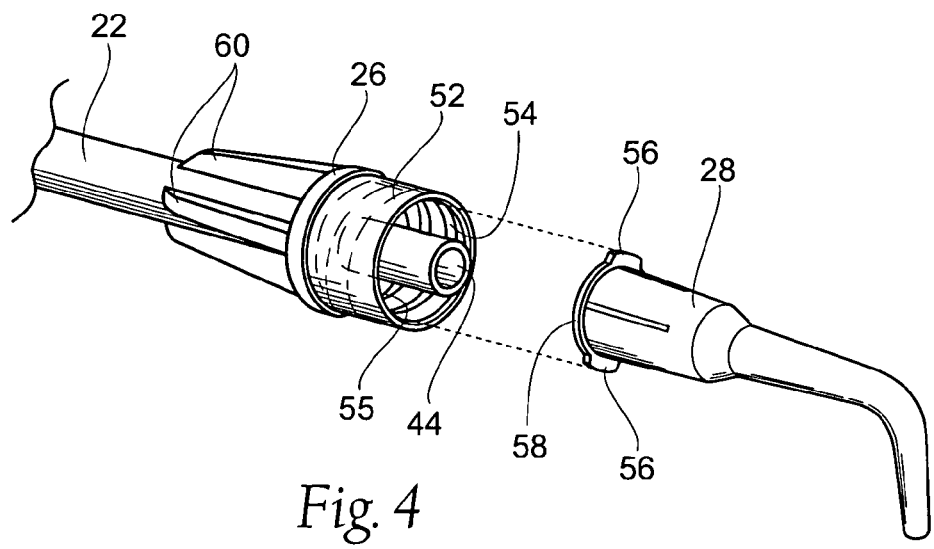
FIG. 4 is an exploded view of an extension member and a connectable dental tip according to the teachings of the present invention.

Referring to FIG. 4, a cut-away exploded perspective view of the extension member 22 and the dental tip 28 is shown. The second end portion 26 of the extension member 22 includes an adaptive releasable locking member, which includes a cuplike portion 52 having an internally threaded surface 54 comprising a raceway 55. The cuplike member 52 should be considered to include any structure that will provide an internal threaded surface that will allow mating with the dental tip 28 and should not be limited to the presently shown design. The threaded surface 54 interacts with a pair of diametrically opposed extending tabs or tab portions 56 radially extending from a flange 58 located on the dental tip 28. The threaded surface 54 and the raceway 55 may be arranged to receive a single tab 56, but preferably it will receive two tabs 56. As the dental tip 28 is threaded into the cuplike member 52, the tabs 56 are compressed against the threaded surface 54 to form a fluid tight fitting between the passageway 44 and the interior of the dental tip 58 (see FIG. 1). When the dental tip 28 is threaded into the cuplike member 52, the taper of the dental tip 28 allows for the passageway 44 to be sealed against the inside of the dental tip 28 without necessarily employing other sealing means. Though not necessary, the passageway 44 is shown extending outwardly of the cuplike member 52. The depicted design allows for a shallow cuplike member, since there is less needed length when threading the dental tip 28. The tabs 56 of the dental tip 28 only need to be threaded a few rotations within the raceway 55 to form a fluid tight seal between the passageway 44 and the dental tip 28. However, the passageway 44 may terminate inwardly of the cuplike member 52, or possibly flush with cuplike member 52. The dental tips 28 are generally considered LUER-LOK®-style dental tips. Thus, the present invention provides an efficient, inexpensive device that will allow adaptation between dental handpieces and LUER-LOK®-style dental tips. Provided the dental tip 28 and the extension member 22 are capable of sealing engagement, the design will fall within the scope of the present invention.

FIG. 4 also shows fins 60 extending along the length of the extension member 22. The fins 60 provide support means for the cuplike member 52 and the extension member 22. The fins 60 reduce twisting of the extension member 22 and potential snapping of the extension member 22 when the dental tip 28 is inserted and secured within the cuplike member 52. It should be understood that the support means could take different shapes and forms than the fins 60 shown, provided they reinforce and strengthen the arrangement of the extension member 22. For instance, the support means could be a solid structure encircling the extension member 22, rather than separate fins. Likewise, more or fewer fins than shown could be used with the extension member 22.

Figure 5:
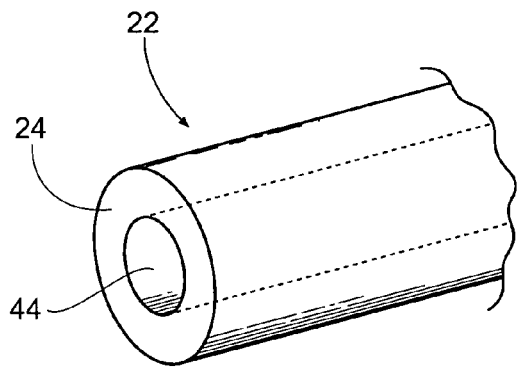
FIG. 5 is cut-away perspective view of an end of an adaptor body according to teachings of the present invention.
Figure 6:
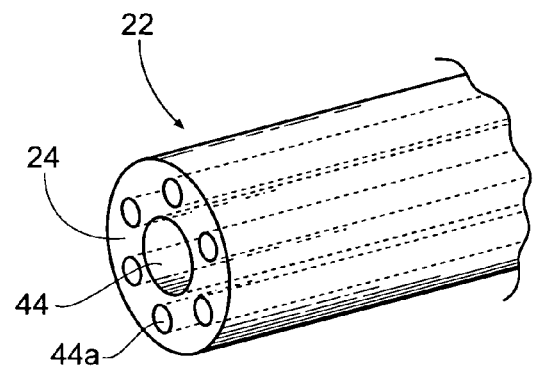
FIG. 6 is a cut-away perspective view of an end of an alternative embodiment of an extension member according to the present invention.

FIGS. 5 and 6 show partial perspective views of the first end 24 of different embodiments of the extension member 22 used in the present invention. FIG. 5 shows the extension member 22 having the single passageway 44, while FIG. 6 shows extension member 22 having the passageway 44 surrounded by a plurality of the secondary passageways 44a. For instance the secondary passageways 44a would allow for mating with the secondary passageway 17 of the handpiece 10 (see FIG. 3). As previously noted, the extension member 22 is not limited to either embodiment, and may also include other potential passageway designs. Whereas the prior art would require many different extension sections or possibly not allow adaptation between different needle or dental tip arrangements, the present invention allows a single extension member to be used for several different dental devices and tips. Furthermore, because the present invention is disposable, using an adaptor to convert between an air/water syringe an air syringe or water syringe is much more economical for many practitioners.

Figure 7:
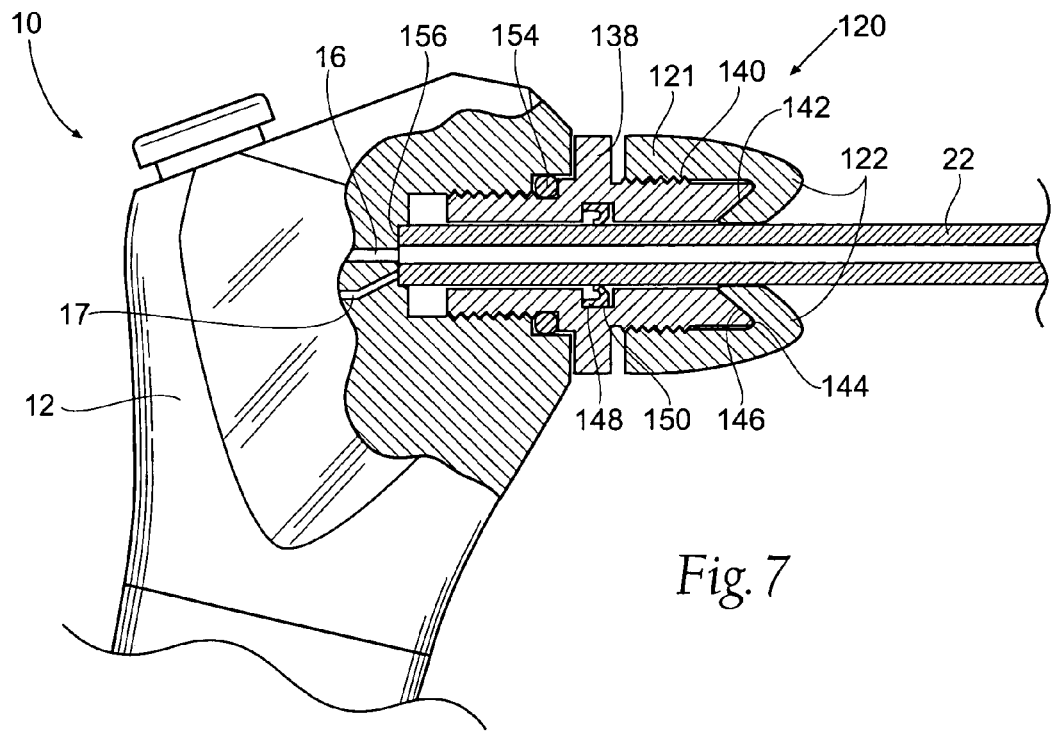
FIG. 7 is a partially cut-away side view of the dental handpiece shown in FIG. 3 and further showing an alternative adaptor assembly for receiving the extension member.

FIG. 7 is a partially cut-away side view of an alternative adaptor assembly 120 for receiving the extension member 22. The adaptor assembly 120 comprises a chuck 121 and a threaded coupling member 138. The chuck 121 comprises a plurality of locking fingers 122 that provide the clamping means needed to retain the extension member 22. Preferably the locking fingers 122 are circumferentially spaced. The coupling member 138 has an externally threaded surface 140 that mates with the chuck 121 and the locking fingers 122 similarly to the first adaptor assembly 20 and chuck 21. The coupling member 138 has distal end 142 that tapers outwardly from the interior of the coupling member 138. The fingers 122 have an inwardly extending ridge 144 that forms a cavity 146. As the chuck 121 is threaded onto the coupling member 138, the distal end 142 of the coupling member 138 will mate with the cavity 146 of the chuck 121. As the chuck 121 is threaded further onto the coupling member 138, the ridges 144 of the fingers 122 come into contact with the sloped or tapered surface of the distal end 142. The ridge 144 will slide inwardly, thereby gripping and retaining the extension member 22. The chuck 121 may be formed out of a resilient material, such as a resilient plastic material, that will allow the chuck 121 to sufficiently grasp the extension member 22 and release it, when necessary. However, other materials may be used to form the chuck 121, as well.

Still referring to FIG. 7, a sealing mechanism 148 is located within a corresponding annular groove 150. The sealing mechanism 148 comprises a circumferential resilient flange to provide further sealing means between the extension member 22 and the coupling member 138. The sealing mechanism 148 also contributes further retention means for the extension member 22 by frictionally engaging the extension member 22 when the extension member 22 is inserted into the coupling member 138. An O-ring 154 located between the coupling member 138 and the socket 14 provides further sealing means, as well. The extension member 22 is inserted into the socket 14 until it abuts an internal surface 156, where it will be in fluid communication with the passageway 16. The overall arrangement provides a fluid-tight arrangement that securely retains the extension member 22.

Figure 8:
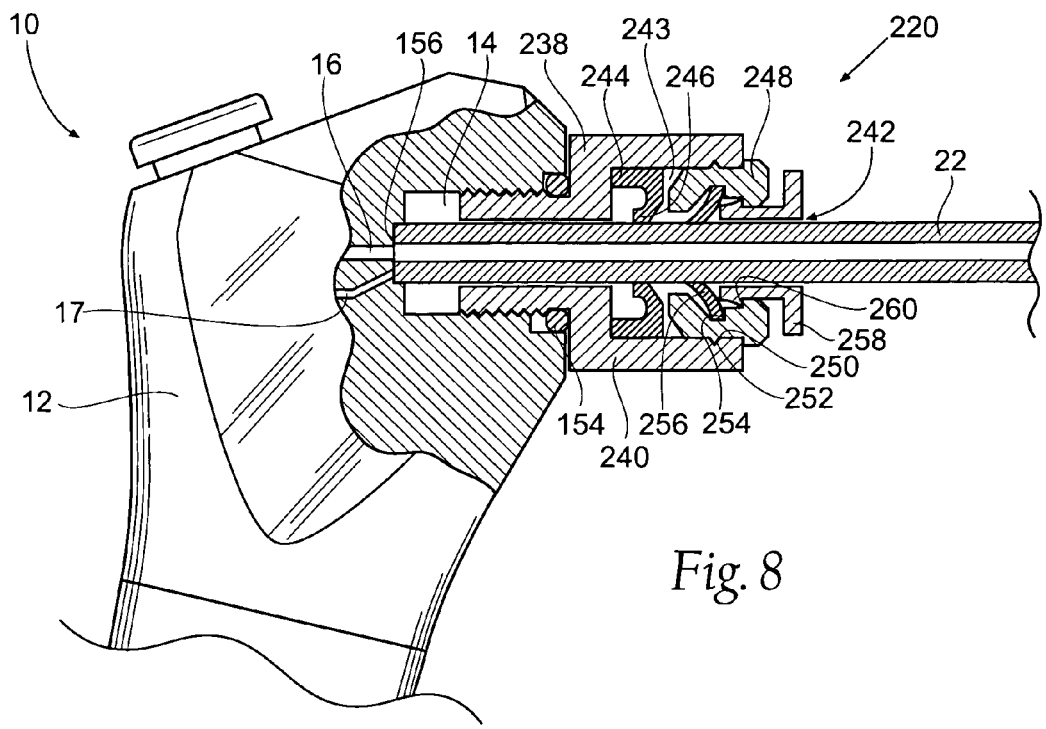
FIG. 8 is a partially cut-away side view of the dental handpiece shown in FIG. 3 and further showing another alternative adaptor assembly for receiving the extension member.

FIG. 8 provides another embodiment of an adaptor assembly 220. As with the prior embodiments, a coupling member 238 is threaded into the socket 14. The coupling member comprises a cylindrical housing 240 with a centrally located throughbore 242 for insertion of the extension member 22. The housing 240 comprises an annular reentrant cavity 243 that surrounds the extension member 22. The extension member 22 will abut the internal surface 156, as was described in FIG. 7 with respect to the assembly 120. Likewise, an O-ring 154 sits between the coupling member 238 and the socket, as shown in FIG. 7.

Still referring to FIG. 8, an annular sealing mechanism 244 having a resilient flange 246 that frictionally engages the extension member to provide fluid-tight retention of the extension member 22 is located within the reentrant cavity 243. A collar 248 is located within the reentrant cavity 243. The collar 248 is connected to the housing 240 by way of a protrusion 250 that mates with a groove 252 located in the housing 240. The collar 248 has an internally located channel 254 for receiving and supporting retention means 256. The retention means 256 preferably comprises a flexible annular disc that surrounds and retains the extension member 22 in frictional engagement. A plunger 258 is retained above the retention means 256 within the reentrant cavity by a lip 260, which is a portion of the collar 248. In a normal position, the retention means 256 exerts upward force on the plunger 258 to retain the plunger 258 against the lip 260. To remove the extension member 22, the plunger 258 is pressed inwardly toward the head portion 12, thereby moving the retention means 256 away from the extension member 22 and allowing the extension member 22 to be removed from the throughbore 242.

Figure 9:
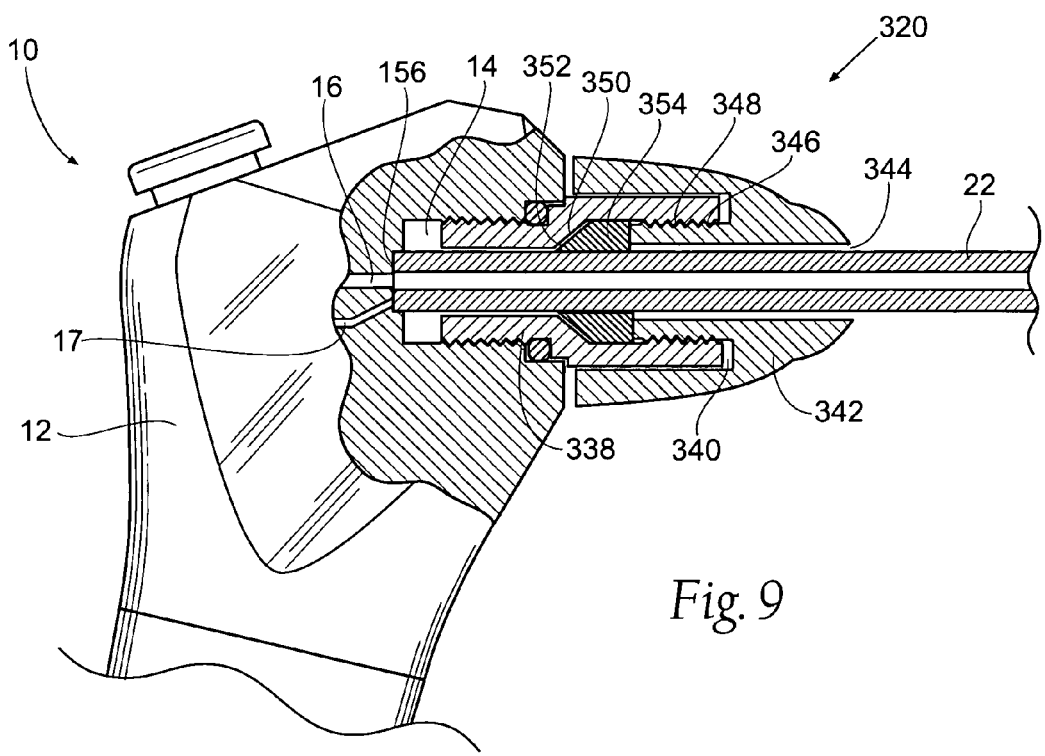
FIG. 9 is a partially cut-away side view of the dental handpiece shown in FIG. 3 and further showing yet another alternative adaptor assembly for the extension member.

FIG. 9 shows another embodiment 320 of an adaptor assembly. The extension member 22 mates with the socket 14, as was shown in FIGS. 7 and 8. A coupling member 338 extends within a reentrant chamber 340 located within an annular collet 342. The collet 342 has a throughbore 344 that surrounds the extension member 22. The chamber 340 is coaxially and radially spaced from the throughbore 344. The chamber 340 has an internally threaded portion 346 that is in threading engagement with an internally threaded portion 348 of the coupling member 338. The coupling member 338 further includes a tapered wall 350. The tapered wall 350 is engageable with a tapered surface 352 of a rubber compression sleeve 354. As the collet 342 is threaded onto the coupling member 338, the compression sleeve 354 is pushed downwardly, which allows the sleeve 354 to slide down the tapered wall 350. The sleeve 354 also moves inwardly towards the extension member 22 to thereby clamp and retain the extension member 22.

As FIGS. 7-9 show, the extension member 22 can be used with a variety of adaptor assemblies, which further enhances the utility of the present invention. Further, FIGS. 7-9 include the secondary passageway 17 within the handpiece 10. If the extension member was arranged as shown in FIG. 6, any of the shown adaptor assemblies would accommodate a secondary fluid through passageway 17. Thus, the adaptability and interchangeability of the present invention is further exemplified.

Figure 10:
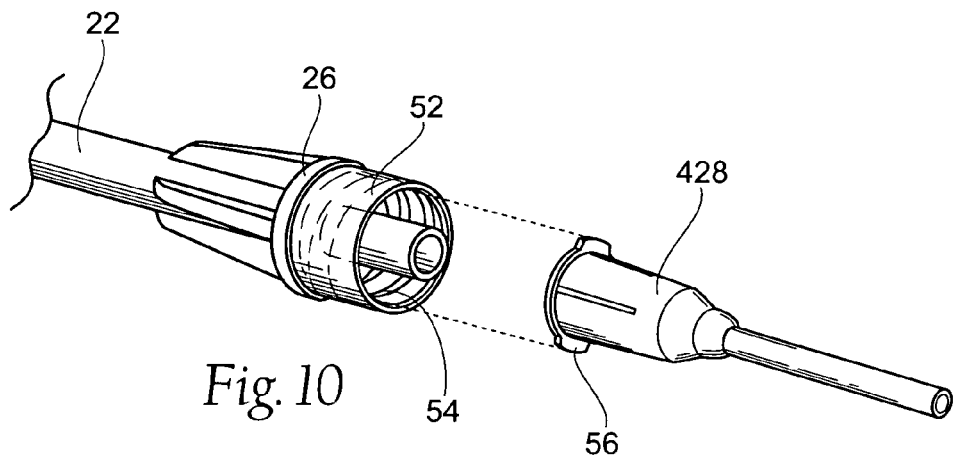
FIG. 10 is a perspective exploded view of an adaptor body as shown in FIG. 4 in arrangement with an alternate dental tip.
Figure 11:
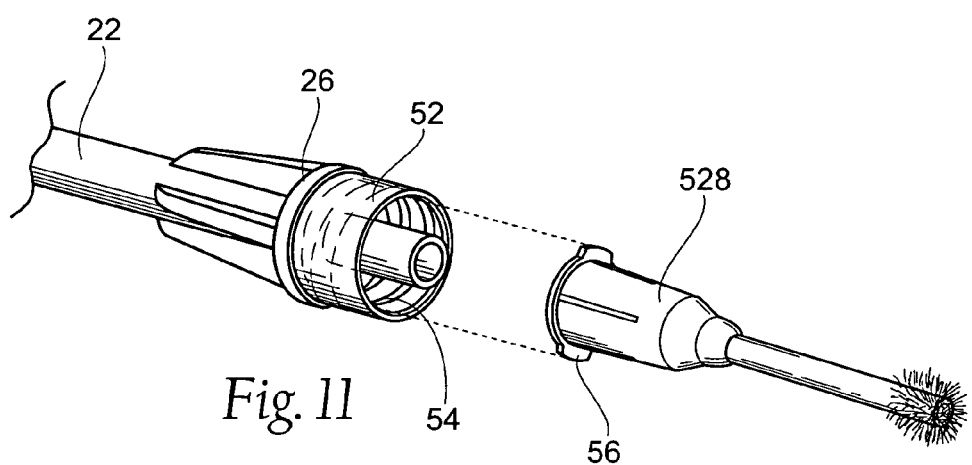
FIG. 11 is a perspective exploded view of an adaptor body as shown in FIG. 4 in arrangement with another alternate dental tip.
Figure 12:
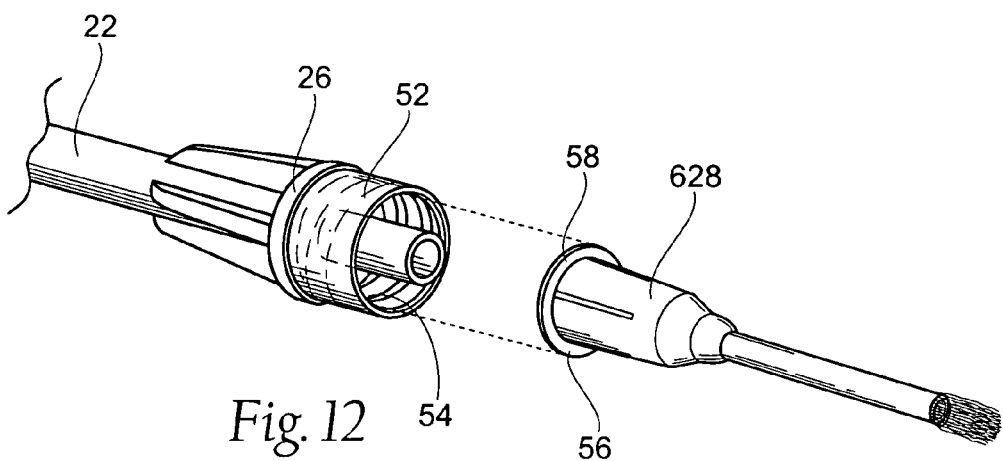
FIG. 12 is a perspective exploded view of an adaptor body as shown in FIG. 4 in arrangement with a further alternate dental tip.

FIGS. 10-12 show exploded views of the second end portion 26 of the extension member 22 and alternative dental tips, 428 (FIG. 8), 528 (FIG. 9), and 628 (FIG. 10). FIGS. 8-10 illustrate that the present invention may be used in conjunction with numerous tip designs. For instance the dental tip 628 has the tabs 56 integral with the flange 58 and not as separate protrusions. Provided the mating portions of the dental tips interact with the threaded portion 54 of the cuplike member 52 to form a fluid tight seal, the present invention is useful for different dental tips. The dental tips 428, 528, and 628 are generally considered LUER-LOK®-style dental tips, and, also, dental tips considered to have LUER tapers. Thus, the present invention provides an efficient, inexpensive device that will allow adaptation between dental handpieces and LUER-LOK®-style dental tips or LUER taper style dental tips.

The present invention provides an affordable extension member for various dental tips and designs. Because the extension member is disposable, it is inexpensive to design and, also, limits possible contamination, since it may be discarded after a single use. The extension member may be used with many different dental handpieces having different gripping means and adaptor assemblies, which further increases the utility of the instrument. The adaptor assemblies described in the present invention also contain new and novel concepts that enhance the utility of the present invention.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. An adaptor assembly for coupling a dental handpiece to an elongated dental extension member, said handpiece having a head portion, said head portion including a socket having a hollow bore in fluid communication with a fluid source, said assembly comprising:

a coupling member having an inwardly extending portion threadably engageable with a mating threaded portion of said socket, said coupling member further comprising a cylindrical housing having a coaxially spaced throughbore for receiving said extension member, said coupling member further including an annular reentrant cavity capable of surrounding said extension member;

annular resilient sealing means received by said reentrant cavity within said housing, said sealing means capable of being in frictional contact with said extension member;

a collar secured to said housing, said collar having an internally located channel;

annular retention means for slidably and sealingly retaining said extension member within said throughbore, said retention means supported within said channel of said collar, said retention means comprises a flexible annular disc, said disc frictionally retaining said extension member in said throughbore; and a plunger having an annular opening capable of surrounding said extension member and arranged for inward movement with respect to said head portion and in contact with said retention means for axial movement of said retention means for temporary release of said retention means.

2. An adaptor assembly according to claim 1, wherein said annular resilient sealing means comprises a resilient cylindrical member positioned inwardly of said flexible annular disc and having a resilient end wall defining an inwardly extending flanged opening frictionally engageable with the exterior surface of said extension member.

* * * * *